United States Patent
Popescu

(10) Patent No.: US 6,862,299 B2
(45) Date of Patent: Mar. 1, 2005

(54) METHOD AND SYSTEM FOR GALVANICALLY ISOLATED TRANSMISSION OF GIGABIT/SEC DATA VIA A SLIP RING ARRANGEMENT

(75) Inventor: Stefan Popescu, Erlangen (DE)

(73) Assignee: Siemens Aktiengesellschaft, Münich (DE)

( * ) Notice: Subject to any disclaimer, the term of this patent is extended or adjusted under 35 U.S.C. 154(b) by 848 days.

(21) Appl. No.: 09/833,950

(22) Filed: Apr. 12, 2001

(65) Prior Publication Data

US 2002/0172228 A1 Nov. 21, 2002

(51) Int. Cl.[7] .................................................. H04J 3/06
(52) U.S. Cl. ........................... 370/516; 370/503; 378/4; 378/15; 378/21
(58) Field of Search ................................ 370/516, 503, 370/304, 507, 517–520, 103, 105.3; 378/15, 17, 4, 91, 10, 21, 62, 87, 901; 348/36, 37; 434/262

(56) References Cited

U.S. PATENT DOCUMENTS

| | | | | |
|---|---|---|---|---|
| 4,644,573 A | * | 2/1987 | Palermo et al. | ................ 378/15 |
| 5,018,174 A | * | 5/1991 | Collins | ........................... 378/4 |
| 5,208,581 A | * | 5/1993 | Collins | ....................... 340/671 |
| 5,402,461 A | * | 3/1995 | Kudo | ........................... 378/15 |
| 6,437,656 B1 | * | 8/2002 | Guynn et al. | ............. 333/24 R |
| 6,765,566 B1 | * | 7/2004 | Tsao | ........................... 345/419 |

OTHER PUBLICATIONS

"Jitter Specifications and methods for Jitter Measurements of Bit–Serial Signals Conforming to Recommendations ITU–R BT.656, ITU–R BT.799 and ITU–R BT.1120," ITU–R Recommendations, Broadcasting Service (Television), Nov. 30, 1998, pp. 152–188.

Media Access Control (MAC) Parameters, Physical Layer, Repeater and Management Parameters for 1000 Mb/s Operation, IEEE Draft P802.3z/DS.0, May 6, 1998.

* cited by examiner

*Primary Examiner*—Wellington Chin
*Assistant Examiner*—Jamal A. Fox
(74) *Attorney, Agent, or Firm*—Schiff Hardin LLP

(57) ABSTRACT

In a data transmission system, and a method for transmitting data in the gigabit/second range, data are transferred from a source located on a rotary part to a stationary part via a slip ring system. A first gigabit data link proceeds from the source at the rotary part to a rotary module of the slip ring system, from which the data are transferred to a stationary module of the slip ring system. From the stationary module of the slip ring system, the data are transferred via a second data link to a receiver. Each of the rotary module and the stationary module of the slip ring system has a clock regenerator. The clock regenerators are operated to synchronize the gigabit/second data, proceeding from the first data link and proceeding to the second data link, to a stable reference clock, so as to prevent jitter from proceeding from the source to the receiver.

20 Claims, 4 Drawing Sheets

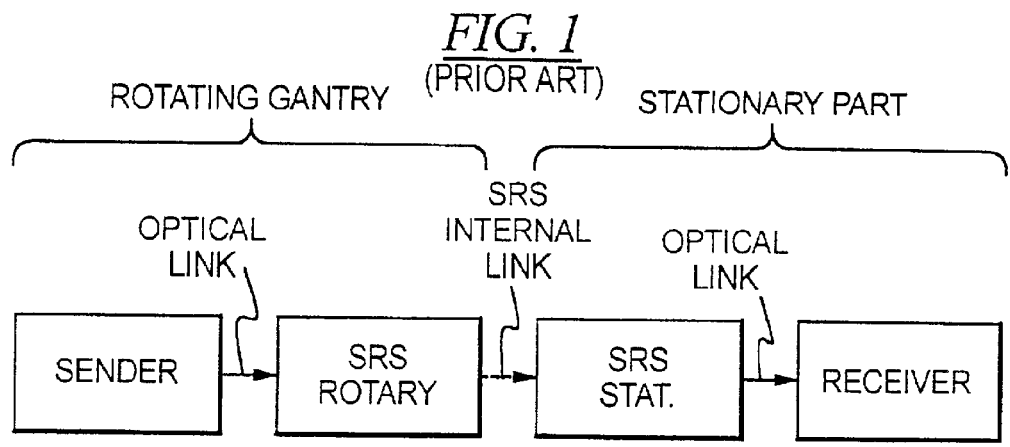
FIG. 1
(PRIOR ART)
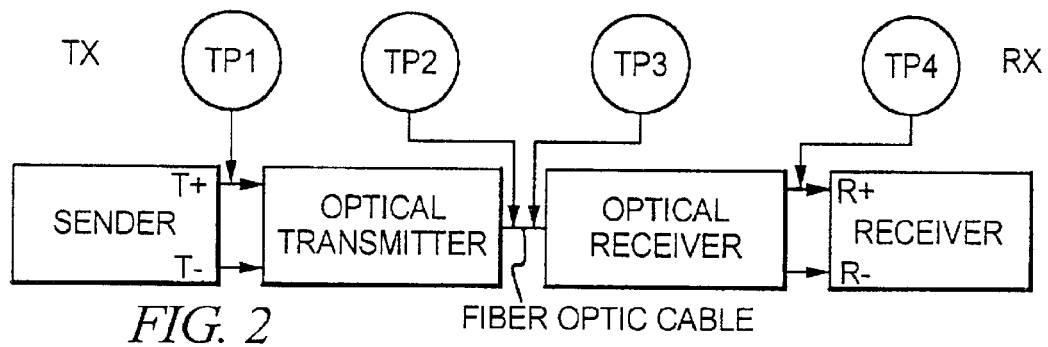
FIG. 2
(PRIOR ART)
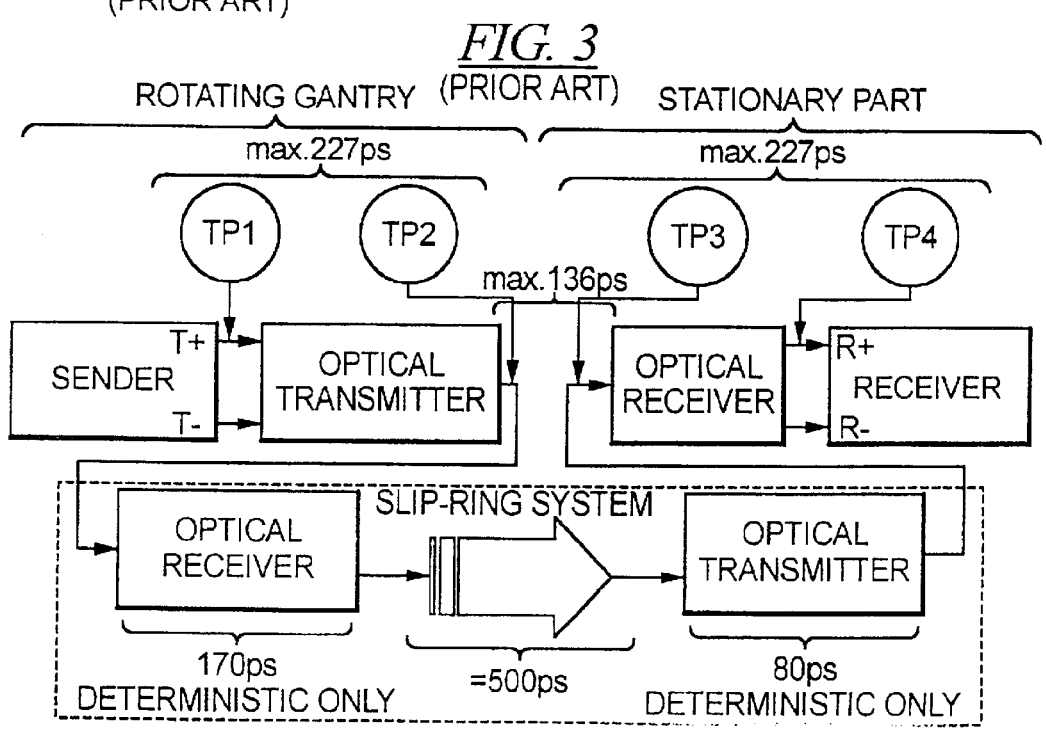

METHOD AND SYSTEM FOR GALVANICALLY ISOLATED TRANSMISSION OF GIGABIT/SEC DATA VIA A SLIP RING ARRANGEMENT

BACKGROUND OF THE INVENTION

1. Field of the Invention

The present invention is directed to a method and a system for transmitting data in the gigabit/sec range in a galvanically isolated manner, such as via a slip ring arrangement, particularly between the rotating gantry and the stationary data processing arrangement of a computed tomography apparatus.

2. Description of the Prior Art

Medical imaging devices, such as computed tomography systems of the third generation, use slip rings to transfer the measurement data from the data measurement system (DMS) which is located on the continuously rotating gantry to the stationary imagery construction system (IRS). The DMS must be electrically isolated from the rotating gantry to avoid leakage currents and electromagnetic interference from perturbing the noise-sensitive measurement channels of the DMS. Additionally, the IRS should be electrically isolated from the gantry so as to avoid electrical hazards to the operator with respect to the high voltages that are employed to operate components on the gantry, as well as to avoid electromagnetic interference produced by the gantry from disturbing the IRS, and electromagnetic interference produced by the IRS from disturbing the gantry components.

Newer computed tomography systems employ a two-dimensional detector array in the DMS, and thus are able to measure more slices per rotation. As an example, the Siemens Somatom Volume Zoom last generation CT scanner acquires four slices simultaneously, thereby producing measurement data at a rate of about 200 Mbit/sec. New clinical applications an even further increase in the number of simultaneously measured slices, which increases the data rate which must be transferred from the DMS to the IRS into the gigabit/sec range.

Transferring data serially in the gigabit/sec range from the data source to the data destination is particularly difficult when using successively connected (chained) communication links, because of jitter accumulation. Jitter is a generic term for the effect of random or deterministic shifts of one to zero transitions and zero to one transitions in the binary data within a serial bit stream that are not quite in phase with the reference clock. These shifts are visible as deviations from the mean phase which occurs in the so called eye diagram. Within a data transmission link, each component transfers the jitter received at its input and adds further, internally generated jitter at its output. The quality of a data link can be assessed by the amount of jitter which occurs at the output end of the link, because it is at this location where a clock and data recovery (CDR) circuit must correctly decode the bits. In spite of jitter, the CDR circuit must provide a satisfactory bit error rate (BER). In addition to jitter, noise injected into the link and pulse distortions due to non-linery components further degrade the overall BER. ITU-T recommendations specify the limits for jitter transfer, jitter generation and jitter tolerance (see ITU-R BT.1363, "Jitter Specifications and Method for Jitter Measurements of Bit-serial Signals").

In a computed tomography system, usually the data source includes an optical transmitter that emits the measurement data serially to the slip ring system (SRS), where a rotary reception module converts the incoming optical bit stream into an electrical signal. The electrical signal is transmitted to the stationary SRS module, either by capacitive coupling or optically using a high-power laser. The stationary SRS module converts the signal received from the rotary part into an electrical bit stream and transmits it further to the receiver via an optical transmitter to the data consumer (destination). Such a known arrangement is schematically shown in FIG. 1 herein.

Therefore, the SRS functions as a transmission channel that is transparent to high-level protocol that behaves as a logical segment of the communication link. In order for the link to function, it must be insured that the jitter contribution of all components between the sender and receiver is sufficiently low so that the receiver is still able to decode the incoming bit stream with a reasonable BER. This requirement can be achieved in a satisfactory manner for data rates below 200 Mbit/sec using standard components.

For gigabit links (>1,000 Mbit/sec), IEEE standards specify the communication link jitter budget and how it is distributed along the link components in IEEE Draft P802.3z/D5.0, May 6, 1998, "Supplement to Carrier Sense Multiple Access with Collision Detection (Csma/cd) Access Method & Physical Layer Specifications-Media Access Control (Mac) Parameters, Physical Layer, Repeater and Management Parameters for 1,000 Mb/s Operation." Section 38.5 of this specification lists the jitter margins as well as the required measurement set-up. As shown in FIG. 2 herein, this standard defines four compliant points TP1, TP2, TP3 and TP4 at which jitter is specified, and three link segments that may add additional jitter, namely TP1 to TP2, TP2 to TP3 and TP3 to TP4.

The jitter budget is distributed according to the following table:

| Compliance Point | Total jitter [ps] |
|---|---|
| TP1 | 192 |
| TP1 to TP2 | 227 |
| TP2 | 345 |
| TP2 to TP3 | 136 |
| TP3 | 408 |
| TP3 to TP4 | 266 |
| TP4 | 599 |

Numbers in the above table represent a high-frequency jitter (above 500 kHz) and do not include low frequency jitter or wander that occurs inherently due to rotation in the case of slip ring transmission.

FIG. 3 herein shows the gigabit link decomposition from the point of view of jitter, when using a slip ring system between the sender and the receiver, and the available and realizable jitter budget. As shown in FIG. 3, additional jitter-producing components exist by virtue of the inclusion of the slip ring system (SRS) between the standard compliance points TP2 and TP3. The optical components of the SRS modules exhibit a deterministic jitter, for which typical figures are shown in FIG. 3. Moreover, the slip ring internal transmission contributes additional jitter. For example, a capacitive slip ring set-up operating experimentally at 400 MHz without rotation, and outside of the usually noisy environment of a CT gantry, exhibited about 500 ps total jitter only for the electrical transmission itself. According to these values, the SRS generates overall approximately 600 ps jitter, which is far beyond the allowable limit of 136 ps. Therefore, data transmission in the gigabit/sec range via an isolated slip ring arrangement using standard components and known techniques is unsuitable, due to the excess jitter. Even attempting to employ extremely fast optical components to reduce the jitter would not overcome this problem, because the overall link, due to the presence of the capacitive slip-ring transmission arrangement, would still be subject to additional externally injected noise.

SUMMARY OF THE INVENTION

It is an object of the present invention to provide a method and system for transmitting data in the gigabit/sec range in a galvanically isolated manner which satisfies the aforementioned specifications for this type of data transmission.

It is a further object of the present invention to provide such a data transmission method and arrangement for transmitting data between a moving part, such as a rotating part, at which a source of gigabit/sec data is disposed, to a data destination which is stationary relative to the moving part.

A further object of the present invention is to provide a data transmission method and system suitable for transmitting gigabit/sec measurement data from a detection system mounted on a rotating gantry in a CT apparatus to a stationary image reconstruction system, via a slip ring system, which satisfies the aforementioned jitter specifications.

The above objects are achieved in accordance with the principals of the present invention in a data transmission system and method wherein gigabit/sec data are to be transmitted from a data source, locating on a rotary part, to a stationary part via a slip ring system, wherein a first gigabit data link proceeds from the source at the rotary part to a rotary module of the slip ring system, with a first clock regenerator connected between the first data link and the rotary slip ring module, wherein a second gigabit data link proceeds from a stationary module of the slip ring system to the data destination at the stationary part, with a second clock regenerator connected between the stationary slip ring module and a second data link, and wherein the first and second clock regenerators operate in combination to synchronize the gigabit/sec data proceeding from the first data link and the gigabit/sec data proceeding to the second data link, to a stable reference clock so as to prevent the jitter from proceeding from the source to the destination.

In one embodiment, the first and second clock regenerators are serial clock regenerators, and in a further embodiment, the first and second clock regenerators are parallel clock regenerators.

The rotary or rotating part can be the gantry of a CT apparatus, in which case the gigabit/sec data source is the radiation detector, and the gigabit/sec data are measurement data obtained by the radiating and examination subject with x-rays from an x-ray source, with the attenuated x-rays being incident on and measured by the detector. In this embodiment, the stationary part is the image reconstruction system, which reconstructs an image of the examination subject from the measurement data supplied thereto via the slip ring system.

DESCRIPTION OF THE DRAWINGS

FIG. 1, as noted above, is a block diagram of a conventional galvanically isolated data transmission arrangement, employing a slip ring system for data in the Mbit/sec range.

FIG. 2, as noted above, is a block diagram of a gigabit link identifying compliant points for jitter according to IEEE standards.

FIG. 3, as noted above, illustrates, with further details for the slip ring system, the known arrangement of FIG. 1 with jitter being measured at the compliant points indicated by the IEEE standards in FIG. 2.

DESCRIPTION OF THE PREFERRED EMBODIMENTS

Figure 4:
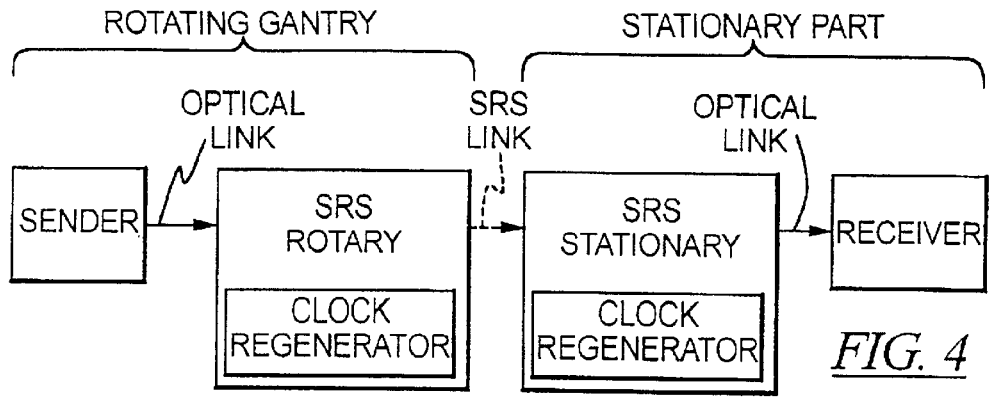
FIG. 4 is a block diagram of an arrangement for transmission of data in the gigabit/sec range constructed and operating in accordance with the principles of the present invention.

The basic components of a system for transmitting data in the gigabit/sec range in accordance with the invention are shown in FIG. 4. The arrangement includes components located on a rotary part, such as a rotating gantry of a CT apparatus, and components located at a stationary part, such as an image reconstruction system of the CT apparatus. The gigabit/sec data are transmitted between the components on the rotating gantry and the components located at the stationary part via a slip ring system (SRS). The SRS has a rotating module, referred to in FIG. 4 as SRS rotary and a stationary module, referred to in FIG. 4 as SRS stationary. The gigabit/sec data are generated at a location designated sender in FIG. 4, which may be, for example, a detector system of the CT apparatus which generates measurement data resulting from radiation of an examination subject with an x-ray source. The gigabit/sec data are transmitted from the sender to the SRS rotary via an optical link at the rotating gantry. After transmission via the SRS, the data are supplied from the SRS stationary via another optical link to a data destination, designated as a receiver in FIG. 4. The receiver can be, for example, a data processing chain and computer system of a CT apparatus which process the gigabit/sec data in a known manner to reconstruct an image of the examination subject.

To solve the aforementioned jitter accumulation problem, the inventive arrangement shown in FIG. 4 employs clock and data regenerators, referred to in FIG. 4 as clock regenerators, in each of the SRS modules, i.e. a clock regenerator at the SRS rotary and a clock regenerator at the SRS stationary. The clock regenerator at the SRS rotary eliminates the jitter accumulated in the transmission from the sender to the SRS rotary (which need not be a direct transmission). The clock regenerator at the SRS stationary eliminate the jitter produced by the SRS transmission itself and thus allows accurate decoding of the received data at the receiver.

The clock regenerators remove the jitter by synchronizing the data to a stable reference clock, and thus prevent the jitter from moving from one link to another.

Figure 5:
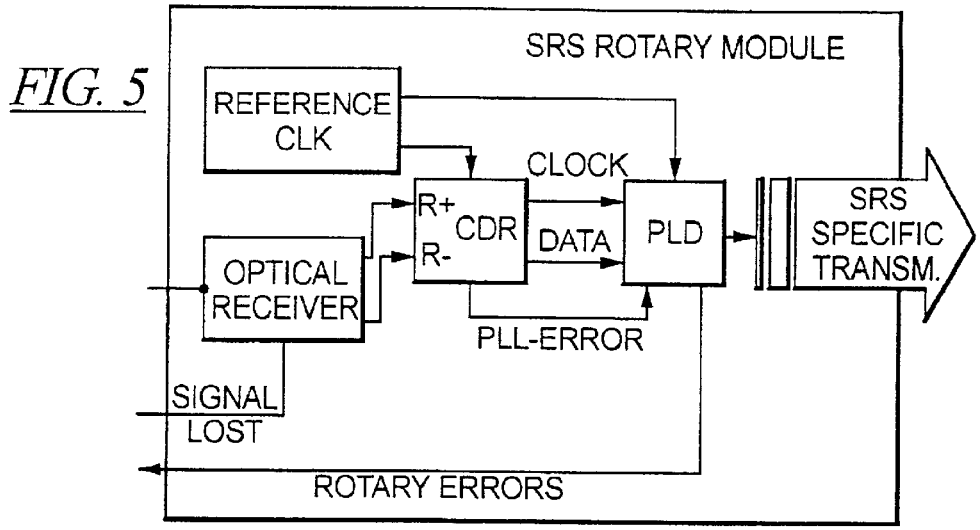
FIG. 5 is a block diagram of the slip ring system rotary module in an embodiment of the invention employing serial clock regenerators.
Figure 6:
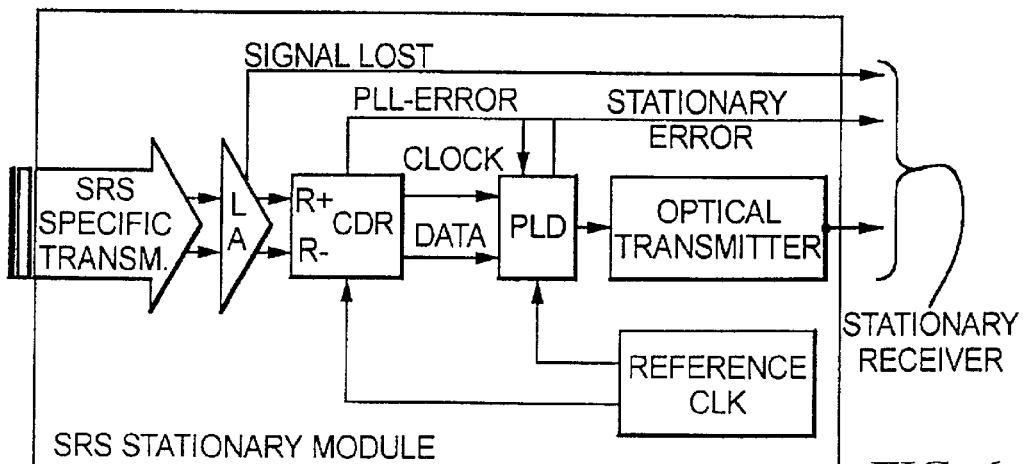
FIG. 6 is a block diagram of the slip ring system stationary module in an embodiment of the invention employing serial clock regenerators.

In one embodiment shown in FIGS. 5 and 6, serial clock regenerators are employed. This embodiment employees standard clock and data recovery circuits to eliminate the high-frequency jitter which is present in the bit stream. The clock recovery unit, such as a PLL, removes high frequency jitter form the data using a low pass filter. The PLL is also able to track a large amount of low frequency jitter (such as drift or wander) below its bandwidth. The low frequency jitter, however, does not affect the operation of the link.

The basic components of the SRS rotary module in the embodiment of employing serial clock regenerators are shown in FIG. 5. The SRS rotary module receives the optical bit stream via an optical receiver, which is able to detect a "signal lost" status and, if so, informs the sender of this status. The optical receiver converts the incoming optical bit stream into a corresponding electrical bit stream, which is supplied to a clock and data recovery (CDR) circuit, such as an integrated circuit chip.

The CDR circuit decodes the electrical bit stream, and provides the data bits and the recovered clock that is free of high frequency jitter. The PLL error is detected and supplied together with the clock and data signals to a programmable logic device (PLD). The PLD re-synchronizes the data with the supplied clock and processes any PLL errors. Such re-synchronization occurs by both the CDR circuit and the PLD being operated by the same stable reference clock. the PLD supplies the outgoing data to the transmitting elements of the SRS rotary module. This data may still be subject to a small amount of low frequency jitter and wander.

Alternatively, the PLD can transmit the data synchronously to the reference clock. In this case, the frequency of the local clock must be set slightly higher than the input clock to avoid losing bits of data. If a negligible BER can be tolerated, the module can use the same frequency-matched clock sources.

The components of the SRS stationary module, shown in FIG. 6, operate in a similar manner. The SRS transmission elements receive the data from the transmission elements of the SRS rotary module. The received data are supplied to a limiting amplifier, which also has the ability to indicate a "signal lost" status to the stationary receiver. The electrical bit stream from the limiting amplifier is processed by the CDR circuit at the SRS stationary module to obtain the recovery clock and the data bit stream. A PLD identical to the PLD in the SRS rotary module performs re-synchronization and error detection at the SRS stationary module. As in FIG. 5, the CDR and the PLD are shown as being operated by the same reference clock, however, the same modifications with regard to the clock signal can be employed at the SRS stationary module as were discussed above with regard to the SRS rotary module.

The serial clock regenerators used at the SRS modules eliminate the high frequency jitter introduced into the link by the preceding components. The data are thus forwarded with a jitter-free local clock source. In this manner, the internal data link within the SRS has a jitter margin of more than 400 ps, which is equivalent to the link segment form TP1 to TP4 in the above-discussed table. This is easily achievable, even with large diameter slip rings as are conventionally employed in CT systems.

The error detection is improved as a result of the jitter reduction, with the system being able to detect and localize communication errors in each link separately i.e., sender to SRS rotary, SRS rotary to SRS stationary, and SRS stationary to stationary receiver. Each of the rotary sender and the stationary receiver "see" at the other end of the link a standard gigabit partner with the SRS being "invisible", at least as to jitter.

Figure 7:
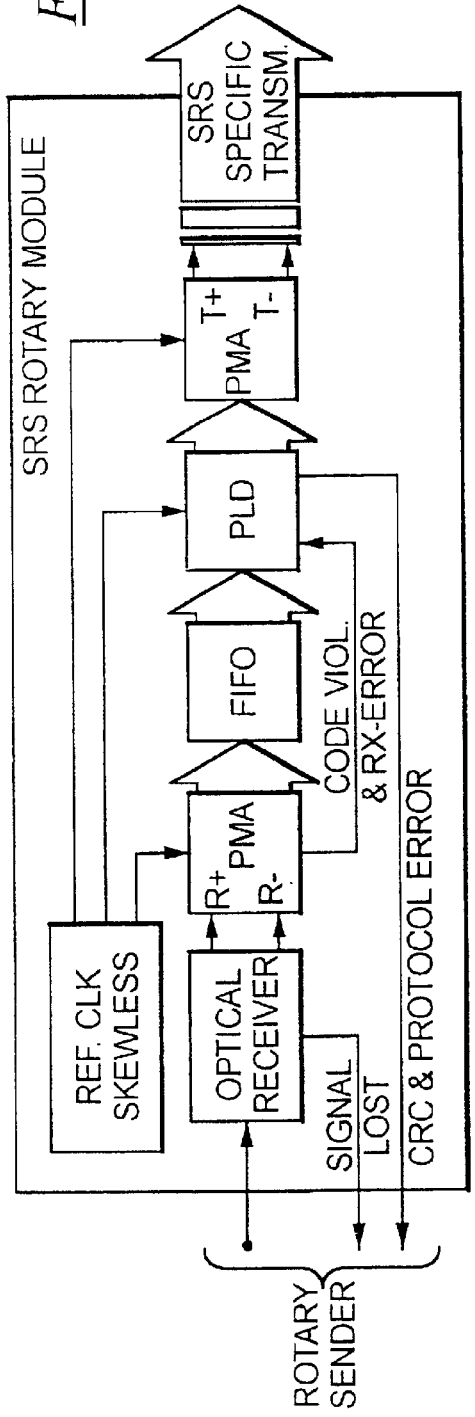
FIG. 7 is a block diagram of the slip ring system rotary module in an embodiment of the invention employing parallel clock regenerators.
Figure 8:
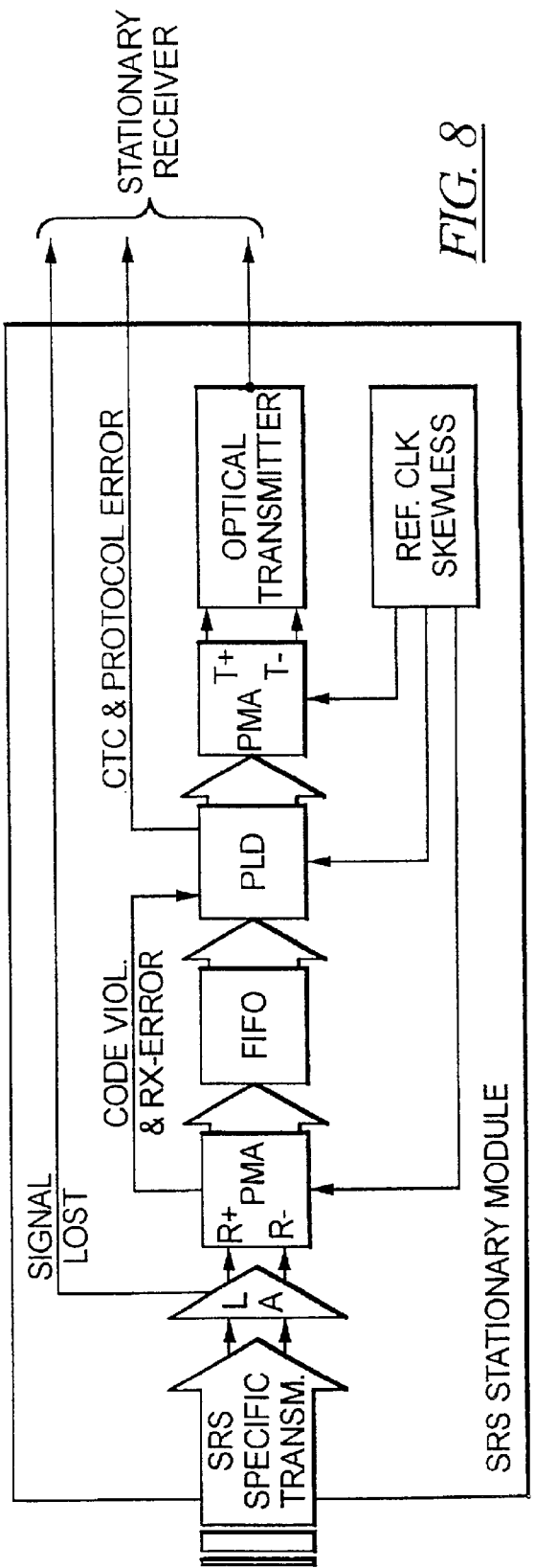
FIG. 8 is a block diagram of the slip ring system stationary module in an embodiment of the invention employing parallel clock regenerators.

FIGS. 7 and 8 show a further embodiment employing parallel clock regenerators. In this embodiment, standard serializer and deserialize (SERDES) devices are employed to recover the data as parallel words, and to re-synchronize the output word and bit stream to a stable reference clock without losses. Each clock regenerator must be able to negotiate between slightly difference clock rates (the recovered clock at the input and the local reference clock at the output). If the local clock is slower than the recovered clock, the regenerator discards some vital words to re-synchronize the data stream. In order to recognize the idle words, each regenerator must know the data format, so that each data packet can be separated, and one idle cycle in between packets can then be discarded, when necessary. The SRS rotary module with a parallel clock regenerator is shown in FIG. 7. As before, the SRS rotary module receives the optical bit stream from the sender with an optical receiver with a "signal lost" status indicator. A PMA-RX circuit decodes the electrical bit stream synchronously to the recovered clock, and packs it into words that are entered into a small FIFO memory. The words, for example, can be 16-bit words. Detected code violations are signaled as errors. A PLD driven with the stable local clock re-synchronizes the word stream to eliminate the jitter. Eventually the PLD discards idle states to avoid overflow of the FIFO memory, if the local clock is slightly lower than the recovered clock. The PLD detects CRC and other protocol errors, and re-sends the words to the serializer PMA-TX circuit. The jitter-free serial bit stream is then sent from the serializer PMA-TX to the transmission elements of the SRS.

The structure of the SRS stationary module employing a parallel clock regenerator is shown in FIG. 8, and is similar to the above-described SRS rotary module of FIG. 7. A limiting amplifier, with the ability to provide a "signal lost" status is supplied with the incoming stream from the SRS reception elements. The bit stream is packed into words which are written into a FIFO memory. A PLD identical to that used in the rotary module shown in FIG. 7 performs re-synchronization and error detection. The words are again serialized into a jitter-free bit stream by the PMA-TX serializer and are converted into optical signals which are sent to the stationary receiver.

By packing the bit stream into parallel words, in the embodiment shown in FIGS. 7 and 8 each SRS module is able to recognize the data packets and to calculate the cyclic redundancy check (CRC) code for each packet. Therefore, error detection and localization are improved compared to the embodiment employing serial clock regenerators shown in FIGS. 5 and 6.

Moreover, the embodiment shown in FIGS. 7 and 8 allows the data stream to be further transmitted, synchronize with the reference clock, without data losses. Therefore, each regenerator also eliminates the low frequency jitter and wander which arise in the preceding link or links. Providing the clock regenerator at the SRS stationary isolates the stationary receiver from the drift and wander low frequency jitter components generated during rotation. This wander jitter is produced by the propagation delay which occurs due to the variable distance between the SRS rotary and the SRS stationary. The wander jitter can amount to more than 4ns, and is purely an SRS side effect.

By using a standard interface to the SRS, different types of slip rings can be used, without having the change the components such as the rotary sender and the stationary receiver. For example, if the SRS cannot transfer data via a single link, the SRS may employ two or more parallel paths by splitting the data stream at the SRS rotary and recombining it into a single string at the SRS stationary. This can be accomplished invisibly to the other components in the system.

The SRS can be any suitable type of assembly for use in CT systems, such as mechanical slip ring assembly, an optical transmission, or a radio frequency transmission system.

Figure 9:
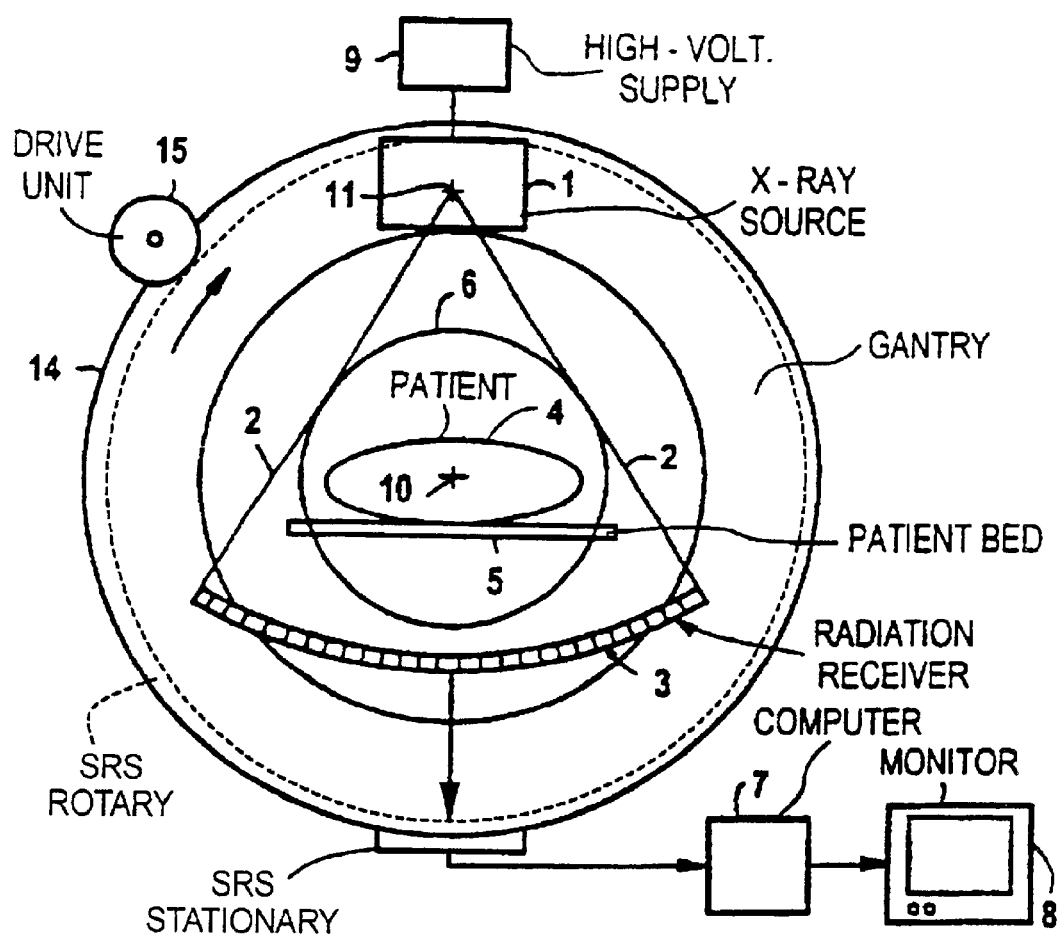
FIG. 9 is a schematic illustration of a computed tomography apparatus employing an arrangement for transmission of data in the gigabit/sec range according to any of the embodiments of the inventive method and system.

FIG. 9 shows the basic components of a computed tomography (CT) system in which any of the above-described embodiments of the gigabit/sec data transmission arrangement can be employed.

The computed tomography system has an x-ray source 1 and a radiation receiver 3 which are mounted on a rotatable gantry 14. The x-ray source 1 is operated by a high voltage supply 9 to emit a fan-shaped x-ray beam 2 from a focus 11. The gantry 14 is rotated in the direction of the arrow by a drive unit 15 so that a patient 4 disposed in an examination volume 6 and lying on a patient bed 5, is irradiated by the x-ray beam 2 from a number of different directions (projections). For each projection, measurement data are produced by the radiation receiver 3 dependant on the attenuated x-rays incident thereon. In the plane of the drawing shown in FIG. 9, the radiation receiver 3 is shown as being composed of a row of detector elements however the radiation receiver 3 will have an extent perpendicular to the plane of the drawing, so that it will be composed of a number of adjacent detector rows. In later generation CT systems, the x-ray beam 2 has an extent along the system axis 10, around which the gantry 14 rotates, so that multiple detector rows can be simultaneously irradiated. In these later generation CT systems, the measurement data produced by the detector 3 are in the gigabit/sec. In FIG. 9, the slip ring system is schematically illustrated by a module on the gantry 14 designated SRS rotary, which rotates with the gantry 14, and a stationary module, designated SRS stationary, which receives the data via the SRS link shown in any of FIGS. 4 through 8. The gigabit/sec data, which have been made jitter-free in accordance with the invention, are supplied to a computer 7 which serves as the receiver described in the various embodiments of the invention. From this data, the computer 7 reconstructs an image of the examination subject 4 in a known manner, which is displayed on a monitor 8.

Although modifications and changes may be suggested by those skilled in the art, it is the intention of the inventor to embody within the patent warranted hereon all changes and modifications as reasonably and properly come within the scope of his contribution to the art.

I claim as my invention:

1. A data transmission system comprising:
   a stationary part;
   a rotary part rotatable relative to said stationary part;
   a source of gigabit/sec data at said rotary part, said data being subject to jitter;
   a slip ring system for transmitting said data from said rotary part to said stationary part slip ring system having a rotary slip ring module at said rotary part and a stationary slip ring module at said stationary part;
   a first gigabit/sec data link proceeding from said source at said rotary part;
   a first clock regenerator connected to said first data link at said rotary slip ring module;
   a receiver for said gigabit/sec at said stationary part;
   a second gigabit/sec data link proceeding to said receiver at said stationary part; and
   a second clock regenerator connected to said second data link at stationary slip ring module, said first and second clock regenerators synchronizing said gigabit/sec data, proceeding from said first data link and proceeding to said second data link, to a stable reference clock to prevent said jitter from proceeding from said source to said receiver.

2. A data transmission system as claimed in claim 1 wherein said first and second clock regenerators are serial clock regenerators.

3. A data transmission system as claimed in claim 2 wherein said jitter includes high frequency jitter, and wherein each of said serial clock regenerators comprises a recovery clock, and a clock and data recovery circuit which eliminates said high frequency jitter by synchronizing outgoing data to said recovery clock.

4. A data transmission system as claimed in claim 2 wherein each of said serial clock regenerators has a local reference clock, and a clock and data recovery circuit which eliminates all of said jitter by synchronizing outgoing data to said local reference clock 5. A data transmission system as claimed in claim 1 wherein each of said first and second clock regenerators is a parallel clock regenerator.

6. A data transmission system as claimed in claim 5 wherein each of said parallel clock regenerators includes a local reference clock and serialization and deserialization circuits which eliminate all of said jitter by synchronizing outgoing data to said local reference clock.

7. A data transmission system as claimed in claim 5 wherein each of said parallel clock regenerators includes a circuit for converting said gigabit/sec data into a plurality of data packets with idle cycles respectively between said data packets, and a synchronization circuit which synchronizes said gigabit/sec data by selectively discarding idle cycles between data packets.

8. A data transmission system as claimed in claim 7 wherein each of said parallel clock regenerators calculates a cyclic redundancy check code for each of said packets, and wherein said parallel clock regenerator at said rotary part transmits said cyclic redundancy check code to said source for use in detecting transmission errors in said first data link and wherein said parallel clock regenerator at said stationary part transmits said cyclic redundancy check code to said receiver for use in detecting transmission errors in said second data link.

9. A data transmission system as claimed in claim 1 wherein said rotary part comprises a computed tomography apparatus gantry having an x-ray source and a radiation detector mounted therein for rotation with said gantry, said radiation detector forming said source of gigabit/sec data and generating said gigabit/sec data dependant on radiation incident on said radiation detector attenuated by an examination subject as said gantry is rotated around said examination subject, and wherein said stationary part comprises an imagery construction system which reconstructs an image of said subject from said gigabit/sec data.

10. A data transmission system as claimed in claim 9 wherein said source of gigabit data comprises a radiation detector having a plurality of parallel rows of radiation detector elements disposed adjacent to each other in a direction parallel to a rotational axis of said gantry.

11. A method for transmitting gigabit/sec data comprising the steps of: providing a stationary part and a rotary part that is rotatable relative to said stationary part;

generating gigabit/sec data at a source at said rotary part, said data being subject to jitter;

transmitting said data from said rotary part to said stationary part via a slip ring system, said slip ring system having a rotary slip ring module at said rotary part and a stationary slip ring module at said stationary part;

transmitting said via said a first gigabit/sec data link at said rotary part said source to said rotary slip ring module;

connecting a first clock regenerator to said first data link at said rotary slip ring providing a receiver for said gigabit/sec data at said stationary part;

transmitting said gigabit/sec data via a second data link at said stationary part proceeding from said stationary slip ring module to said receiver;

connecting a second clock regenerator to said second data link at said stationary slip ring module; and operating said first and second clock regenerators in combination to synchronize said gigabit/sec data, proceeding from said first data link and proceeding to said second data link, to a stable reference clock to prevent said jitter from proceeding from said source to said receiver.

12. A method as claimed in claim 11 comprising providing a first serial cock regenerator as said first clock regenerator and providing a second serial clock regenerator as said second clock regenerator.

13. A method as claimed in claim 12 wherein said jitter includes high-frequency jitter, and comprising the step of, at each of said first and second serial clock regenerators, eliminating said high-frequency jitter by synchronizing outgoing data to a recovery clock.

14. A method as claimed in claim 12 comprising, at each of said first and second serial clock regenerators, eliminating all of said jitter by synchronizing outgoing data to a local reference clock.

15. A method as claimed in claim 11 comprising providing a first parallel clock regenerator as said first clock regenerator and providing a second parallel clock regenerator as said second clock regenerator.

16. A method as claimed in claim 15 comprising, at each of said first and second parallel clock regenerators, eliminating all of said jitter by synchronizing outgoing data to a local reference clock in serialization and de-serialization circuits.

17. A method as claimed in claim 15 comprising, at each of said first and second parallel clock regenerators, converting said gigabit/sec data into a plurality of data packets with idle cycles respectively between said data packets, and selective discarding idle cycles between data packets to synchronize said gigabit/sec data.

18. A method as claimed in claim 17 comprising, at each of said first and second parallel clock regenerators, calculating a cyclic redundancy check code for each of said packets, and transmitting the cyclic redundancy check code calculated at said first parallel clock regenerator to said source for use in detecting transmission errors in said first data link, and transmitting said cyclic redundancy check code from said second parallel clock regenerator to said receiver for use in detecting transmission errors in said second data link.

19. A method as claimed in 11 comprising generating said gigabit/sec data by providing a radiation detector as said source, and irradiating said radiation detection with x-rays with an examination subject disposed in a path of said x-rays so that attenuated x-rays are incident on said radiation detector, while rotating said gantry, to generate measurement data from said detector as said gigabit/sec data.

20. A method as claimed in claim 19 wherein said gantry is rotated around a rotational axis, and comprising the step of providing a radiation detector having a plurality of parallel rows disposed next to each other along said access.

* * * * *